United States Patent
Chen et al.

(10) Patent No.: US 7,938,119 B2
(45) Date of Patent: May 10, 2011

(54) LARYNGEAL MASK AIRWAY WITH A BELT, OPERATING PIECE FOR CONTROLLING THE SAME, AND GAS SUPPLY KIT COMPRISING THE SAME

(76) Inventors: Tien-Sheng Chen, Taipei (TW); Hui-Bih Yuan, Taipei (TW)

( * ) Notice: Subject to any disclaimer, the term of this patent is extended or adjusted under 35 U.S.C. 154(b) by 970 days.

(21) Appl. No.: 11/776,889

(22) Filed: Jul. 12, 2007

(65) Prior Publication Data
US 2008/0236592 A1  Oct. 2, 2008

(30) Foreign Application Priority Data
Mar. 30, 2007  (TW) ................................ 96205250 U (51) Int. Cl.
*A61M 11/00* (2006.01)
(52) U.S. Cl. ................ 128/207.15; 128/200.26
(58) Field of Classification Search .......... 128/207.14–207.16, 200.26; 604/96, 604/96.01, 97.03
See application file for complete search history.

(56) References Cited

U.S. PATENT DOCUMENTS

| | | | | | |
|---|---|---|---|---|---|
| 5,529,582 | A | * | 6/1996 | Fukuhara | 606/205 |
| 5,850,832 | A | * | 12/1998 | Chu | 128/200.26 |
| 5,896,858 | A | * | 4/1999 | Brain | 128/207.15 |
| 7,040,322 | B2 | * | 5/2006 | Fortuna | 128/207.15 |

* cited by examiner

*Primary Examiner* — Steven O Douglas
(74) *Attorney, Agent, or Firm* — Alan Kamrath; Kamrath & Associates PA (57) ABSTRACT

A laryngeal mask airway includes a flexible tubular portion, an inflatable sealing cuff, an inflation tube, and a belt. The flexible tubular portion has a first opening part and a second opening part. The inflatable sealing cuff is disposed surrounding the first opening part. The inflation tube has one end connected to the inflatable sealing cuff and the other end for directing gas into the inflatable sealing cuff. The belt is secured on the first opening part. Moreover, an operating piece controls the laryngeal mask airway, and a gas supply kit includes the laryngeal mask airway.

16 Claims, 11 Drawing Sheets

LARYNGEAL MASK AIRWAY WITH A BELT, OPERATING PIECE FOR CONTROLLING THE SAME, AND GAS SUPPLY KIT COMPRISING THE SAME

BACKGROUND OF THE INVENTION

1. Field of the Invention

The present invention relates to a laryngeal mask airway and, particularly, to a laryngeal mask airway with a belt. Moreover, the present invention also provides an operating piece for controlling the same and a gas supply kit comprising the same.

2. Description of the Related Art

In the case of anesthesia and apnea patients, the top priority is the provision of pulmonary gas by emergency medical personnel. Among the various respiration sustaining instruments, the laryngeal mask airway, due to its ease of operability, is a common alternative to endotracheal intubation.

Figure 1:
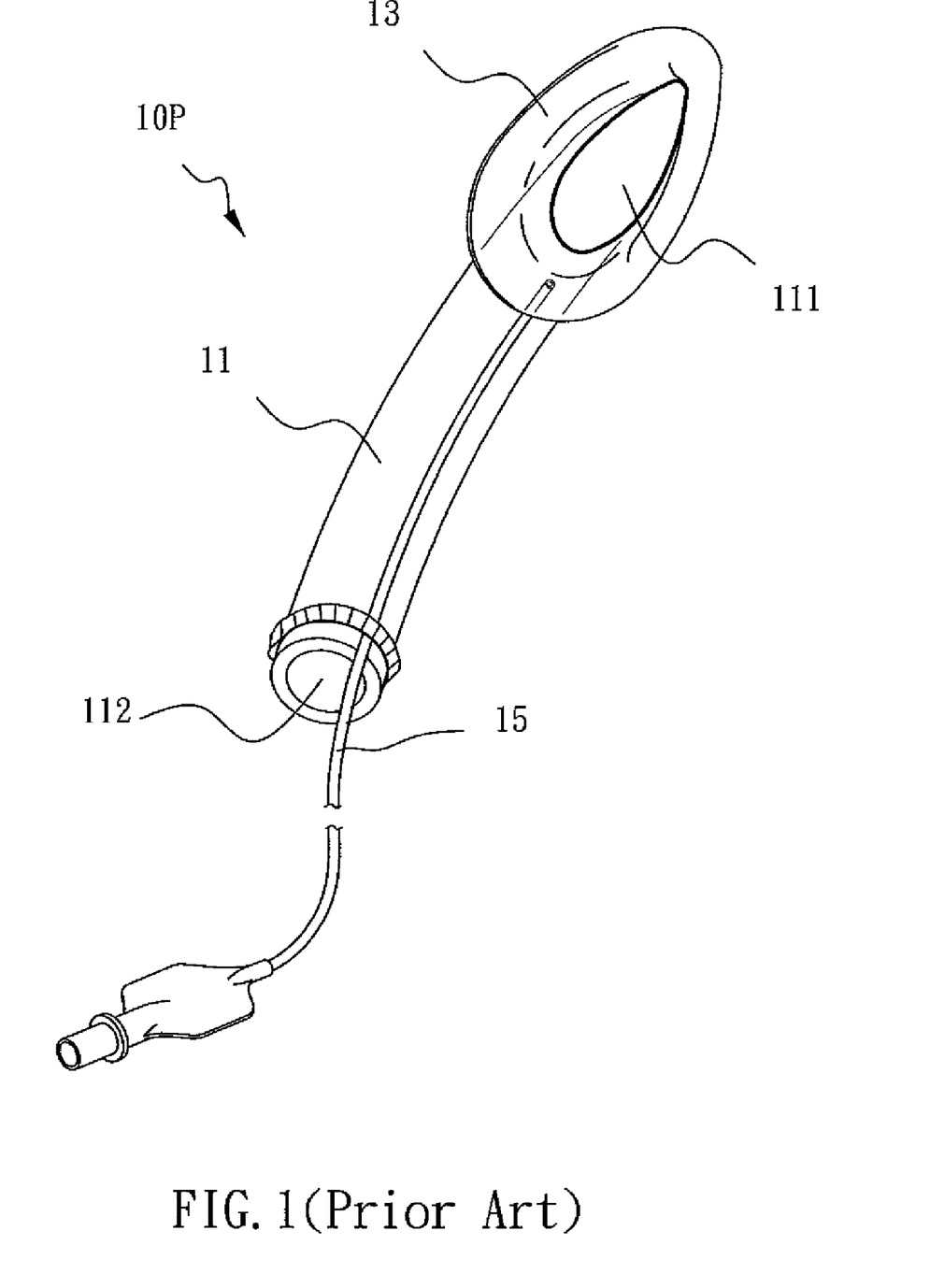
FIG. 1 illustrates the structure of a conventional laryngeal mask airway.

Please refer to FIG. 1 for the structure of a conventional laryngeal mask airway 10P. Basically, the laryngeal mask airway 10P comprises a flexible tubular portion 11, an inflatable sealing cuff 13, and an inflation tube 15. The flexible tubular portion 11 comprises a first opening part 111 and a second opening part 112. The inflatable sealing cuff 13 is disposed surrounding the first opening part 111, and the inflation tube 15 has one end connected to the inflatable sealing cuff 15 and the other end directing gas into the inflatable sealing cuff 13.

Figure 2:
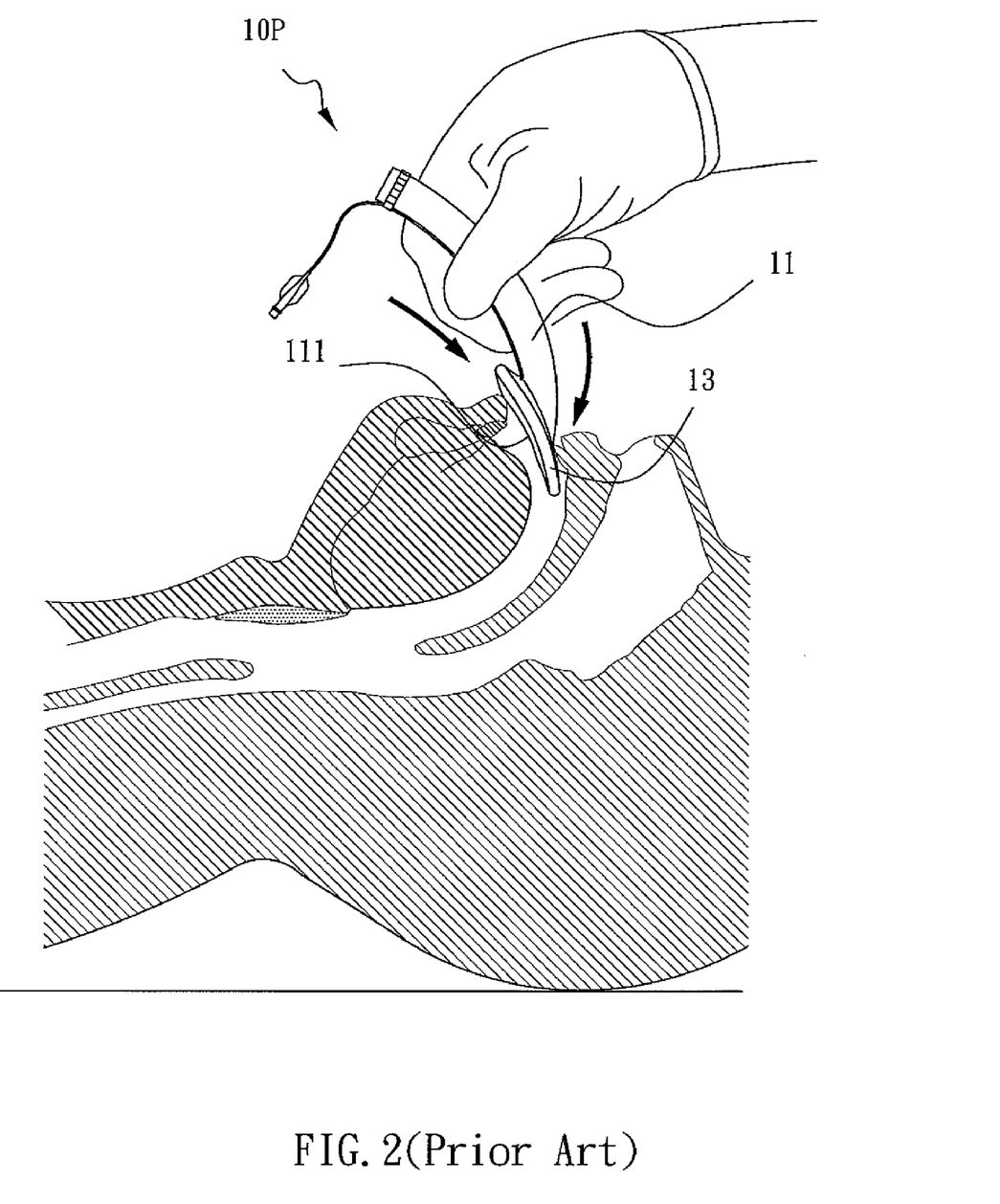
FIGS. 2 to 4 are illustrative diagrams showing the conventional laryngeal mask in use.
Figure 3:
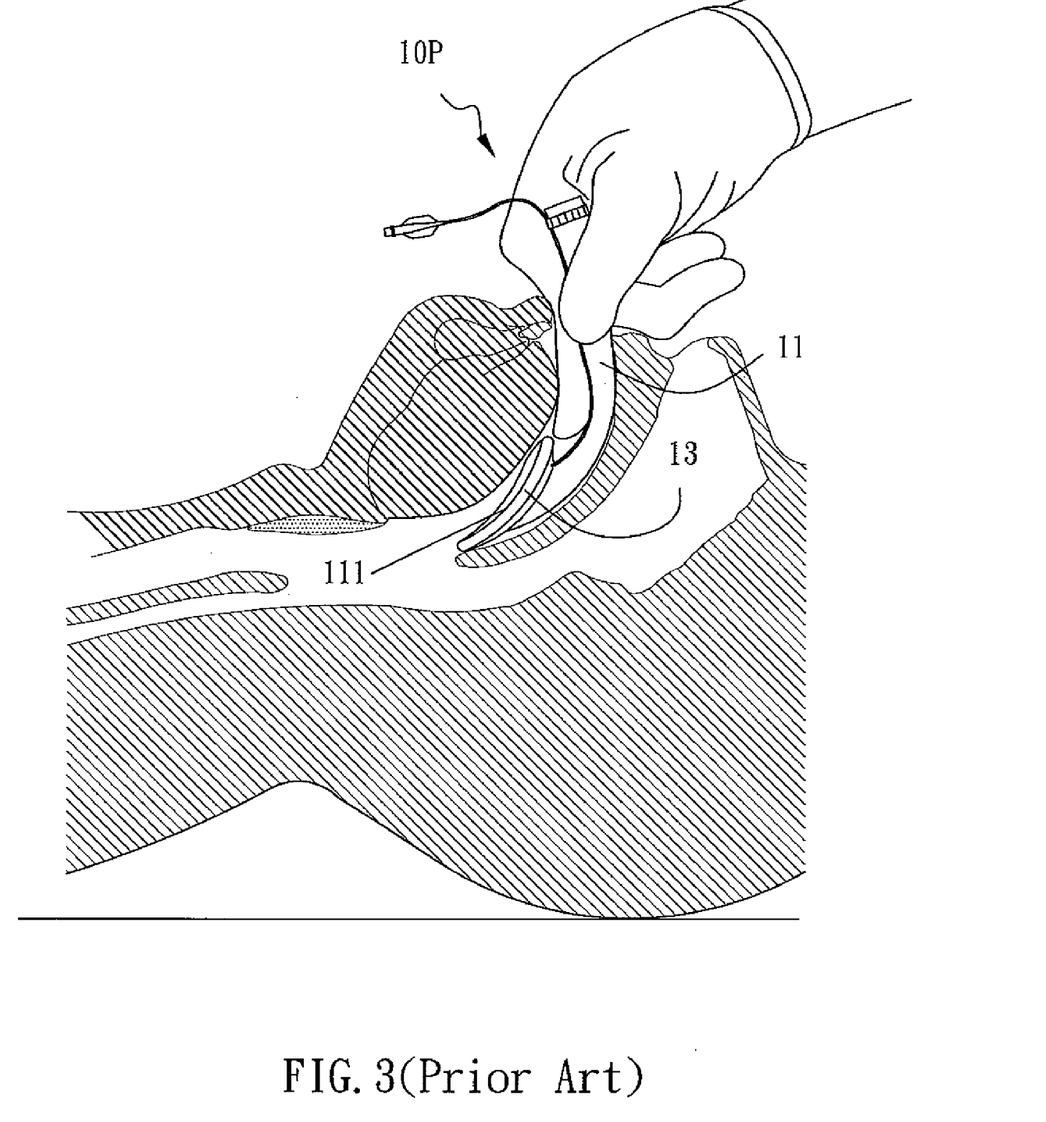
Figure 4:
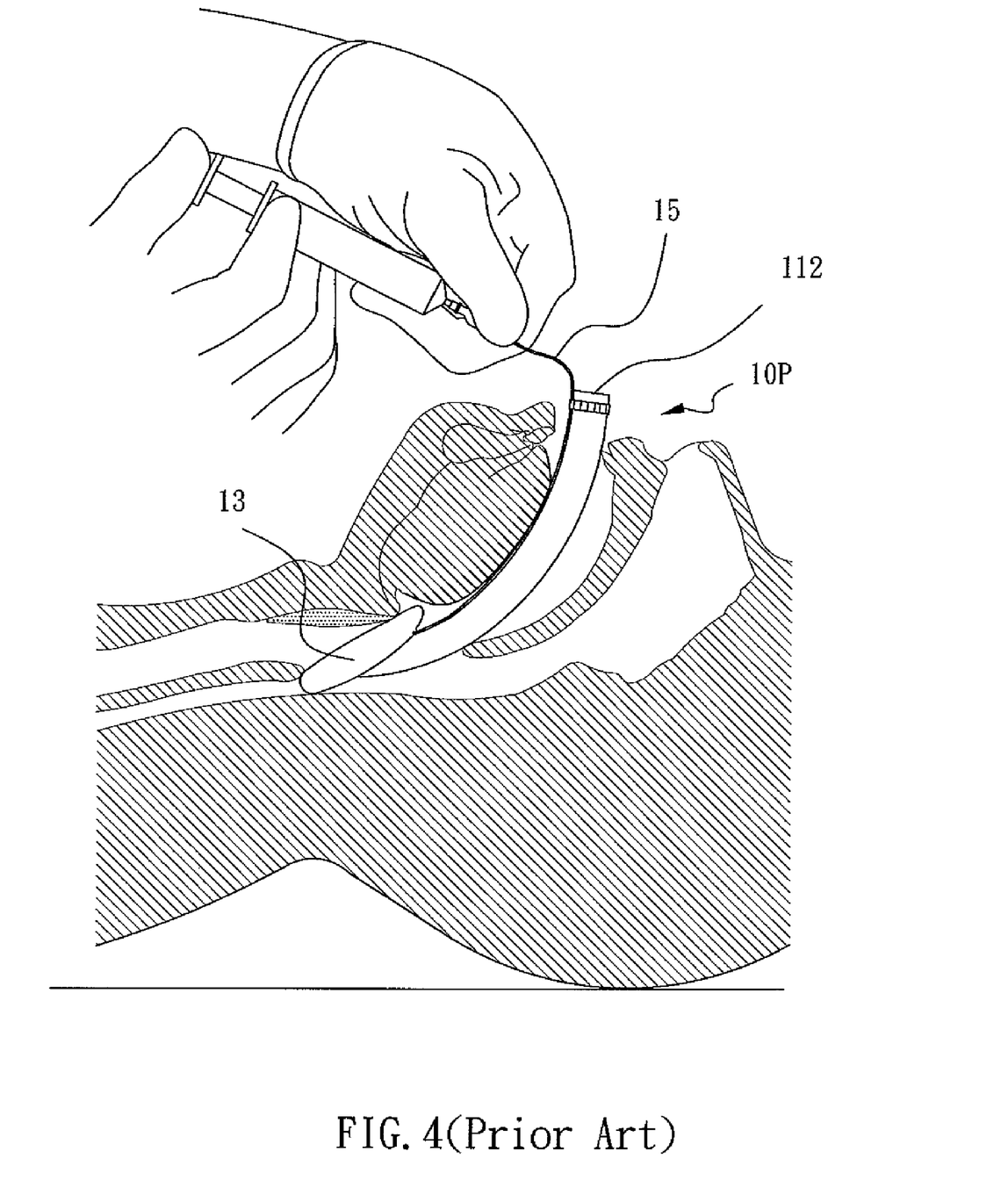

Please refer to FIGS. 2 to 4 for illustrative diagrams showing the conventional laryngeal mask airway 10P in use. First, a user may insert the laryngeal mask airway 10P into a patient's mouth by the end having the inflatable sealing cuff 13, which is in a deflated condition. When the inflatable sealing cuff 13 reaches a deeper part in the mouth, the user will then have to insert his/her finger into the patient's mouth to bend the front end of the laryngeal mask airway 10P, making the structure of the laryngeal mask airway 10P conform with the structure of the patient's upper jaw. In addition, due to the softness of the laryngeal mask airway 10P the user may not exert force thereby. Thus, the user has to push aside the tongue with his/her finger to bend the first opening part 111 and the flexible tubular portion 11 to such an extent that they can pass the upper jaw and reach the opening of the trachea, as shown in FIG. 3. In FIG. 4, when the laryngeal mask airway 10P gets to a specific position, the user may then aerate the inflatable sealing cuff 13 from the inflation tube 15 so as to form a sealing mask in the patient's throat. The sealing mask may encompass the opening of the trachea and form an air passage thereby. After that, the user may direct gas, such as oxygen, from the second opening part 112 to maintain the patient's respiration.

Accordingly, during the installation of a laryngeal mask airway, users always have to insert their finger(s) (especially their index fingers) into a patient's mouth to pass the soft, inconvenient laryngeal mask airway through the upper jaw because of the obstruction of the patient's tongue. In general, this displacement of fingers may cause two problems. First, there will be a risk that the user is bitten by the patient during the installation of a laryngeal mask airway. Second, in a case where a patient's oral space is overly small, which may be caused by an overly small mouth, an overly tight tooth joint, or an overly thick tongue, a user may encounter difficulty inserting his/her finger(s) into the patient's mouth, resulting in a failure of the installation of the laryngeal mask airway.

SUMMARY OF THE INVENTION

It is therefore an objective of the present invention to provide a laryngeal mask airway comprising a belt structure to be pushed by an operating piece (against which force can be exerted with an operating piece) so as to create a bend at the front end of the laryngeal mask airway. In addition, by the use of the operating piece, the laryngeal mask airway may be hardened temporarily, transmitting the force exerted by the user to the front end and providing the laryngeal mask airway of the present invention with the function of a laryngoscope in order to depress the tongue and reach the larynx. Therefore, the laryngeal mask airway of the present invention can eliminate the need for users to insert their fingers into a patient's mouth, and it may be much more workable in cases where the oral space is limited.

It is another objective of the present invention to provide an operating piece used together with a laryngeal mask airway having a belt. One end of the operating piece may be used to apply force to the belt so as to change the shape of the laryngeal mask airway. Furthermore, the curvature of the operating piece is in conformity with the radian of a human oral airway.

It is still another objective of the present invention to provide a gas supply kit which comprises a laryngeal mask airway and an operating piece. When used together, the laryngeal mask airway and the operating piece may eliminate the need for users to insert their fingers into a patient's mouth, thus facilitating the installation process.

To achieve these and other objectives mentioned above, the laryngeal mask airway of this invention comprises a flexible tubular portion, an inflatable sealing cuff, an inflation tube, and a belt. The flexible tubular portion has a first opening part and a second opening part. The inflatable sealing cuff is disposed surrounding the first opening part. The inflation tube has one end connected to the inflatable sealing cuff and the other end directing gas into the inflatable sealing cuff. The belt is secured on the first opening part.

In use, by simply inserting an operating piece into the flexible tubular portion and pressing the operating piece on the belt, users may produce a bending effect similar to the curved blade of a laryngoscope at the end of the inflatable sealing cuff. Therefore, they may consequently depress the tongue when the laryngeal mask airway is bent and pass it through the upper jaw in a style similar to the placement of a laryngoscope. After the laryngeal mask airway enters the larynx, users may then draw back the operating piece to recover the laryngeal mask airway to its original status covering the opening of the trachea. In addition, users may inflate the inflatable sealing cuff from the inflation tube so as to complete the installation of the laryngeal mask airway.

Apparently, due to the design of the belt, as well as the utilization of the operating piece, users may easily install the laryngeal mask airway without inserting their fingers into the patient's mouth. Hence, the laryngeal mask airway of this invention is capable of increasing the safety and convenience of the installation.

Moreover, the operating piece may be a metal bar, which enables users to incorporate it with the laryngeal mask airway having a belt at lower cost while still attaining the same effect mentioned above. In order to satisfy different demands, the operating piece of this invention may also be a hollow tube. One end of the hollow tube may be applied to the belt of the laryngeal mask airway, and users may insert an endoscope or other similar image pickup apparatus into the hollow tube. The endoscope may then emerge from the bore of the tube, allowing users to use an endoscope, an operating piece, and a laryngeal mask airway concurrently to facilitate the observation of a patient's upper airway.

Additionally, the operating piece may also be an image pickup apparatus. Said image pickup apparatus comprises a steel pipe, an image-capturing unit, and a handgrip. The steel pipe comprises a propping end and a handling end, with said propping end being capable of applying pressure to the belt. The image-capturing unit is installed on the steel pipe for capturing images of a patient's upper airway. The handgrip is installed at the handling end and comprises a power supply electrically connected to the image-capturing unit for providing electricity thereto. To make the image pickup apparatus satisfy various users' demands, the image pickup apparatus may further comprise a display unit electrically connected to the image-capturing unit for displaying the image captured by the image-capturing unit. Also, the image pickup apparatus may be installed with a memory unit electrically connected to the image-capturing unit for storing the image captured by the image-capturing unit and a signal emission unit electrically connected to the image-capturing unit for transmitting the image captured by the image-capturing unit to an external display wirelessly.

By using the gas supply kit incorporating a laryngeal mask airway and an operating piece of the present invention, users may obviate the inconvenience arising during the operation as well as reduce the possibility of injury to the user. More importantly, the utilization of different types of operating pieces may meet the needs of different users. Therefore, the present invention may be deemed as a major breakthrough in laryngeal mask airways.

Other objectives, advantages, and novel features of the invention will become more apparent from the following detailed description when taken in conjunction with the accompanying drawings.

BRIEF DESCRIPTION OF THE DRAWINGS

The accompanying drawings, which are included in and constitute a part of this specification, illustrate the embodiments of the invention and, together with the description, explain the features and principles of the invention. In the drawings.

DETAILED DESCRIPTION OF THE PREFERRED EMBODIMENT

To further elaborate the idea behind the present invention, several concrete embodiments are enumerated.

Figure 5:
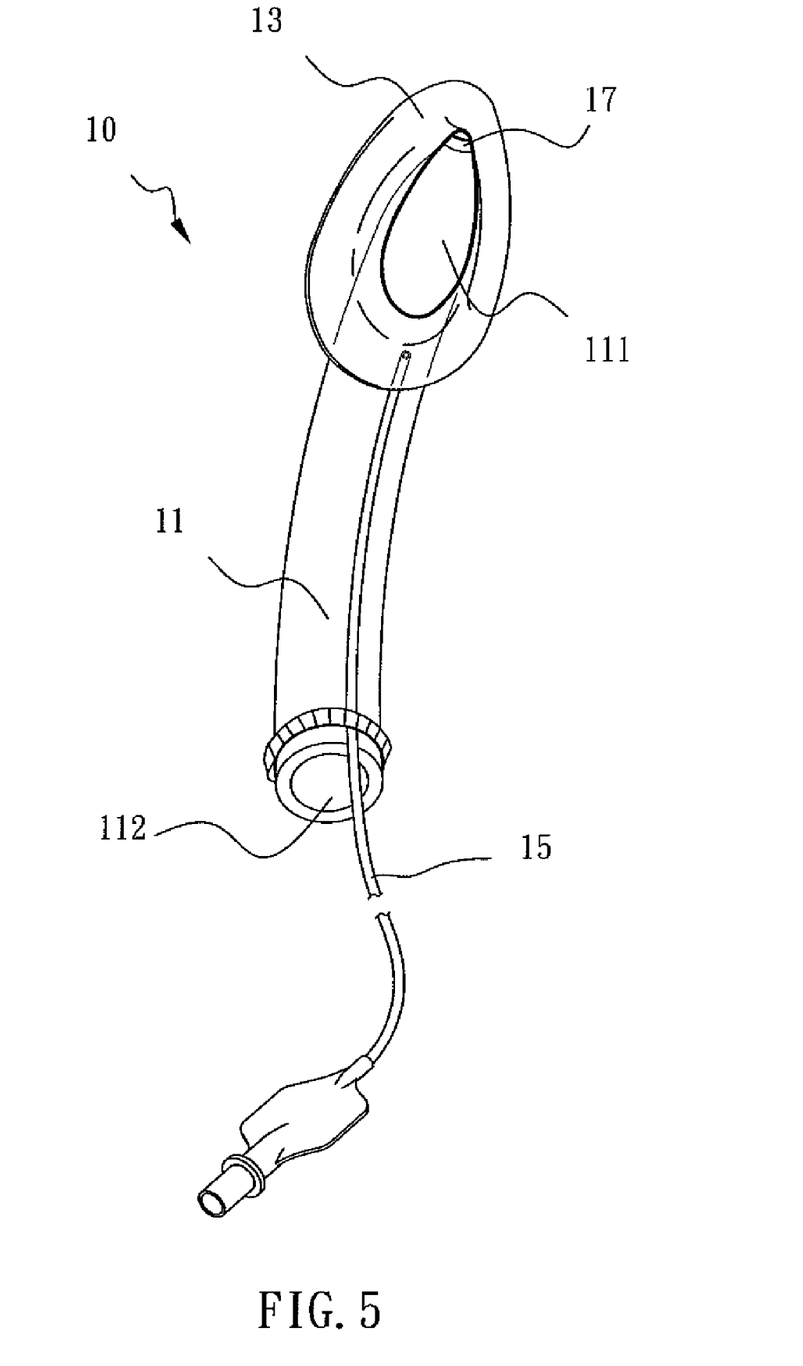
FIG. 5 illustrates the structure of a laryngeal mask airway of the present invention.

Refer to FIG. 5 for an illustration of the structure of a laryngeal mask airway 10 of the present invention. The laryngeal mask airway 10 of this invention comprises a flexible tubular portion 11 comprising a first opening part 111 and a second opening part 112; an inflatable sealing cuff 13 surrounding the first opening part 111; an inflation tube 15 comprising one end connected to the inflatable sealing cuff 13 and the other end directing gas into the inflatable sealing cuff 13; and a belt 17 secured on the first opening part 11. The first opening part 111 corresponds to the portion of the laryngeal mask airway 10 that may cover the trachea opening of a patient. Therefore, the belt 17 may be secured on the inflatable sealing cuff 13 or on the flexible tubular portion 11, and the connection therebetween may be carried out without limitation by adhesive bonding, one-piece shaping, gluing, etc. In order not to affect the gas flux, the position of the belt 17 is close to the tip of the first opening part 111. The belt 17 may also extend therefrom to cover the tip of the first opening part 111. In that case, the shape of the belt 17 is more similar to that of a semi-ellipse than that of a strip.

As shown in FIG. 5, the inflatable sealing cuff 13 may be fabricated into an oval, which may cover the trachea opening of a patient more tightly and reduce the possibility of gas leakage. However, the shape of the inflatable sealing cuff 13 is not limited thereto and it may also be an oval, an ellipse, a circle, or other geometric shape.

Figure 6A:
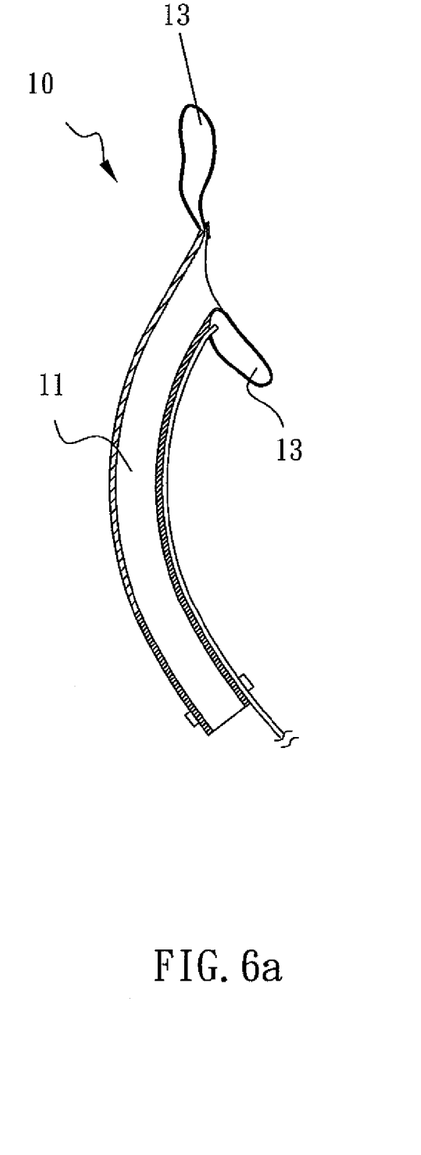
FIGS. 6a and 6b illustrate the laryngeal mask airway of the present invention without and with an operating piece, respectively.
Figure 6B:
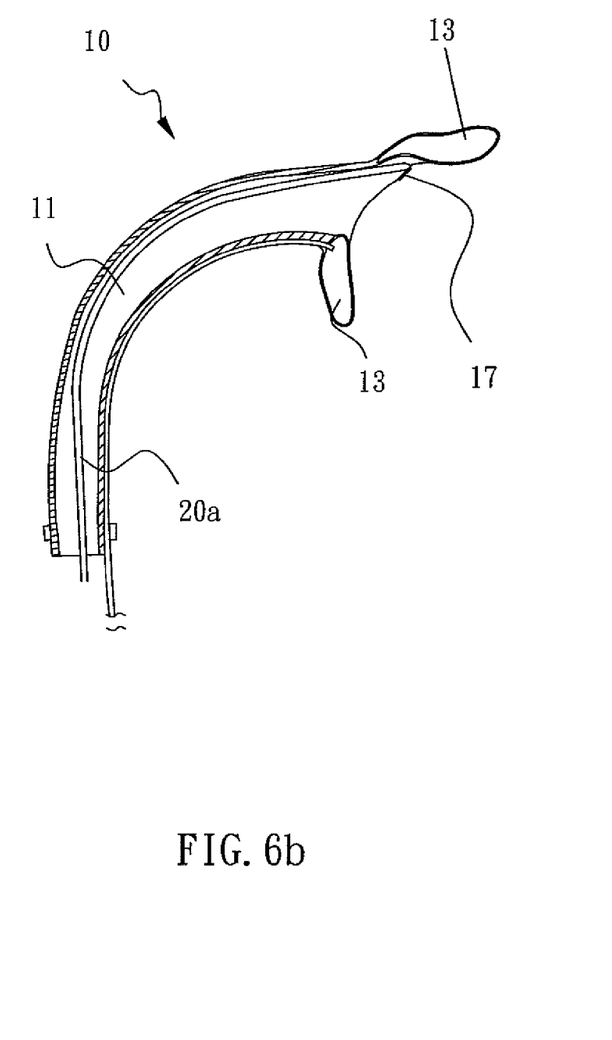

FIGS. 6a and 6b illustrate the laryngeal mask airway 10 of the present invention without and with an operating piece, respectively. As shown in FIG. 6a, when the laryngeal mask airway 10 is used in the absence of an operating piece, the tubular portion 11 is slightly crooked, and the inflatable sealing cuff 13 is not especially bent. In FIG. 6b, the operating piece is a metal bar 20a with a curvature in conformity with the radian of a human oral airway. Thus, when the metal bar 20a is pressed against the belt 17 of the laryngeal mask airway 10, it may bend the inflatable sealing cuff 13. In addition, since the metal bar 20a is harder than the laryngeal mask airway 10, the tubular portion 11 of the laryngeal mask airway 10 may be bent to the extent necessary to fit the radian of a human oral airway when metal bar 20a is inserted into the laryngeal mask airway 10. Therefore, because the laryngeal mask airway 10 has been bent to an ideal extent, users may directly put the laryngeal mask airway 10 inserted by the metal bar 20a into the patient's mouth without using their fingers to press the inflatable sealing cuff 13 of the laryngeal mask airway 10, simplifying the installation of the laryngeal mask airway 10.

Figure 7:
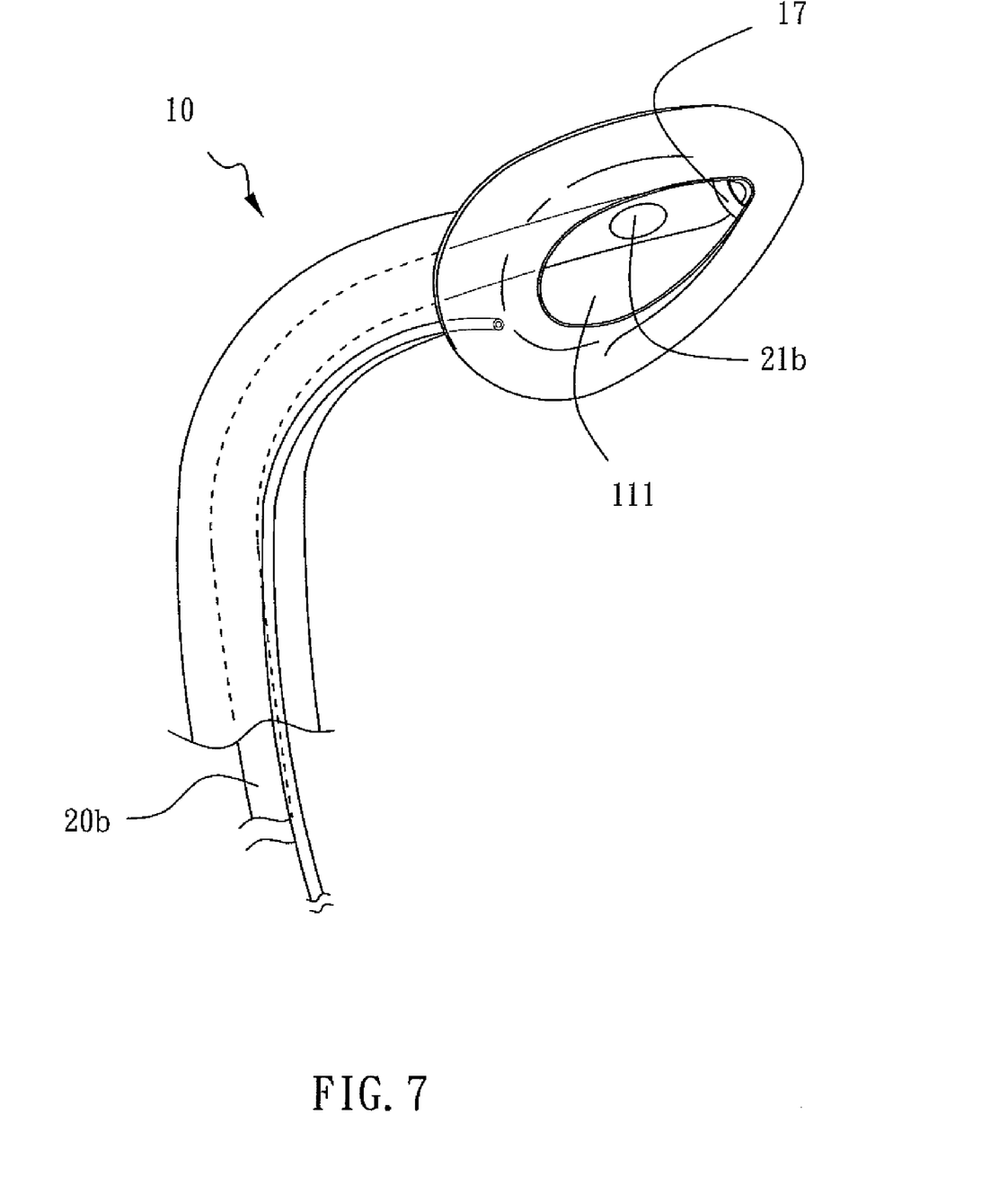
FIG. 7 is an additional illustration showing the laryngeal mask airway of the present invention used with an operating piece.

Refer to FIG. 7 for an additional illustration showing the laryngeal mask airway of the present invention used with an operating piece. In this embodiment, the operating piece is a hollow tube 20b having a bore 21b drilled therein. In use, one end of the hollow tube 20b is pressed against the belt 17, and the bore 21b is located at the first opening part 111 of the tubular portion 11. Since the hollow tube 20b also has a curvature in conformity with the radian of a human oral airway, users may complete the installation without bending the laryngeal mask airway 10 by their fingers. Furthermore, since the operating piece is a hollow tube 20b, users may still apply an endoscope or other image pickup apparatus during the installation of the laryngeal mask airway 10. In that circumstance, the camera lens of the endoscope may emerge from the bore 21b to capture the images so as to provide the users with a better understanding of the patient's upper airway.

Figure 8:
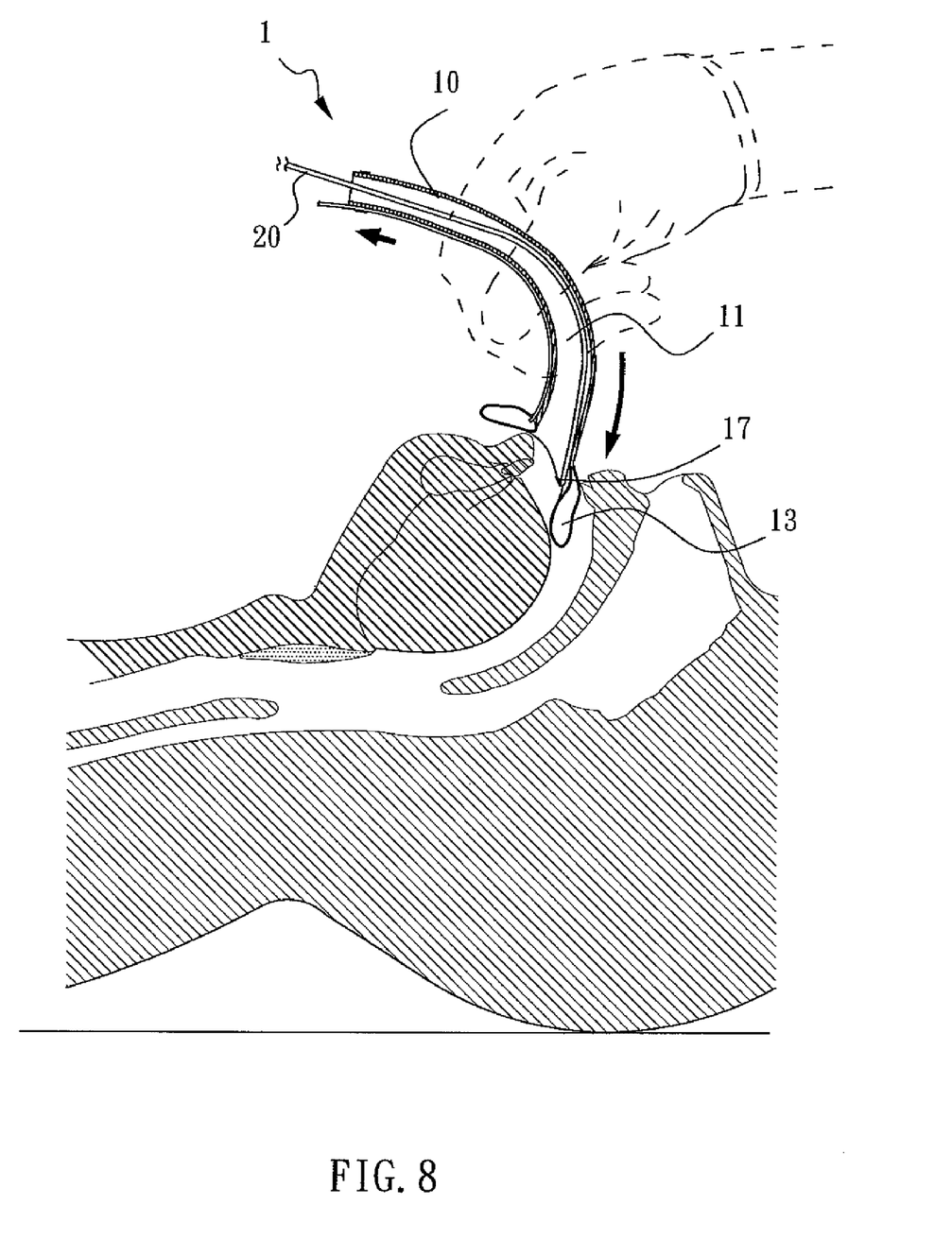
FIG. 8 is an illustrative diagram of the gas supply kit of the present invention in use.

To further illustrate how the laryngeal mask airway 10 is used with the operating piece 20, please refer to FIG. 8 for an illustrative diagram of the gas supply kit 1 of the present invention in use. As shown, before installation, the operating piece 20 is inserted in the laryngeal mask airway 10, and one end of the operating piece 20 is leaned against the belt 17 so as to bend the inflatable sealing cuff 13 of the laryngeal mask airway 10 and the tubular portion 11 properly. Since the laryngeal mask airway 10 has been bent, the direction of the force exerted by a user may vary accordingly. Compared with the conventional style in which the upper jaw of a patient is pushed and pressed, the gas supply kit 1 of this invention may pass through the patient's upper jaw simply by the user's slight rotation of the kit. Meanwhile, since the operating piece 20 has a specific hardness, the gas supply kit 1 of the present invention may be used in the same way as a laryngoscope to push aside and raise the base of the patient's tongue, making the installation easier. When the gas supply kit 1 is approaching the trachea opening of a patient, the operating piece 20 may be drawn back when necessary, or an endotracheal tube may be disposed to the patient's trachea through the operating piece 20. Different consequential processes may be adapted in accordance with the type of the operating piece 20 used.

Figure 9:
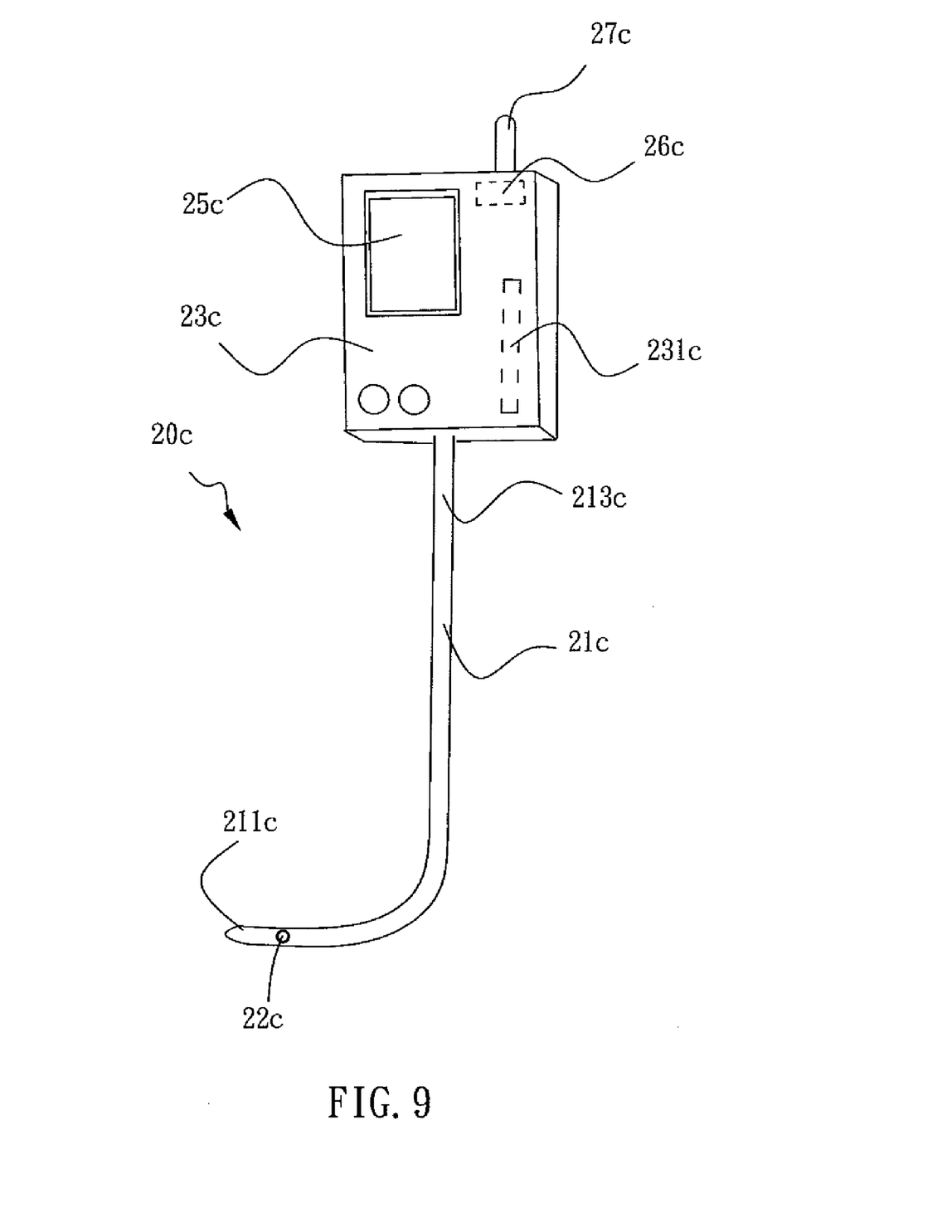
FIG. 9 illustrates the structure of an embodiment of the operating piece of the present invention.

Refer now to FIG. 9 for the structure of another embodiment of the operating piece 20 of the present invention. To equip the operating piece 20 with an image pickup function, the operating piece 20 of the invention may also be an image pickup apparatus 20c. The image pickup apparatus 20c comprises at least the following: a steel pipe 21c comprising a propping end 211c and a handling end 213c, with said propping end 211c being capable of applying pressure to the belt 17 of a laryngeal mask airway 10; an image-capturing unit 22c installed on the steel pipe 21c and being capable of capturing the image of a patient's upper airway; and a handgrip 23c installed at the handling end 213c and comprising a power supply 231c electrically connected to the image-capturing unit 22c for providing electricity thereto. Accordingly, when the image pickup apparatus 20c is used together with a laryngeal mask airway 10 having a belt 17, the steel pipe 21c may lean against the belt 17 of the laryngeal mask airway 10. In the meantime, the curvature of the steel pipe 21c may bend the laryngeal mask airway to the extent in conformity with the radian of a human oral airway. Furthermore, the image pickup apparatus 20c may also comprise a display unit 25c, a memory unit 26c, and/or a signal emission unit 27c. Since all the aforementioned units are electrically connected to the image-capturing unit 22c, users may directly observe the image captured by the image-capturing unit 22c on the display unit 25c to get a understanding of the patient's upper airway. Alternatively, the image captured by the image-capturing unit 22c may also be transmitted by the signal emission unit 27c to an external display 30. In addition, by using the memory unit 26c, the image captured by the image-capturing unit 22c may be temporarily or permanently stored.

Figure 10:
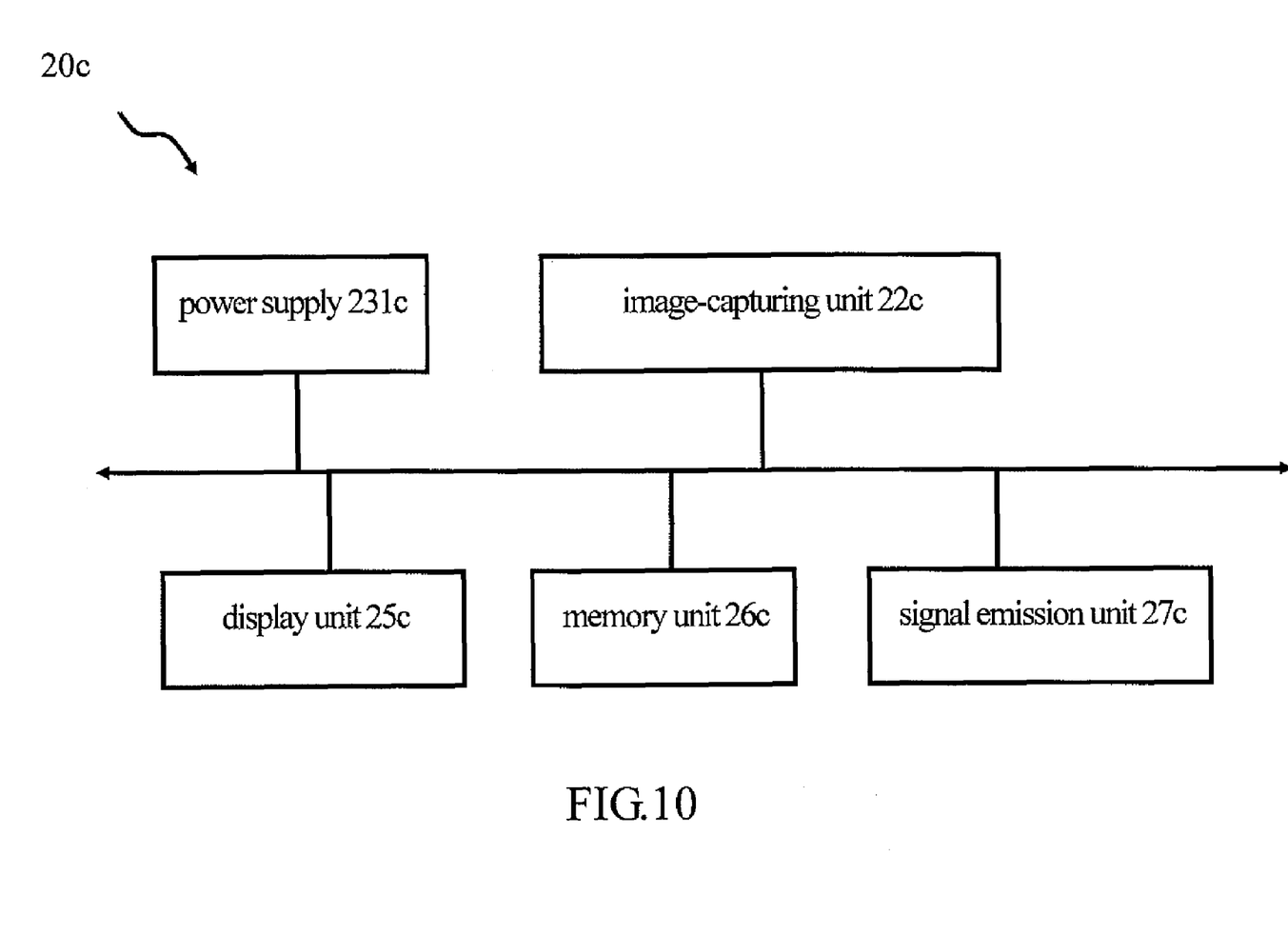
FIG. 10 illustrates the circuit arrangement of an embodiment of the image pickup apparatus of the present invention.

Refer to FIG. 10 for the circuit arrangement of an embodiment of the image pickup apparatus 20c of the present invention. As shown, the image pickup apparatus 20c comprises a power supply 231c, an image-capturing unit 22c, a display unit 25c, a memory unit 26c, and a signal emission unit 27c. The power supply 231c may provide the electricity to other units, and it may be a battery or other power supplying device. The image-capturing unit 22c is installed on the steel pipe of the image pickup apparatus 20c and is capable of capturing the image of a patient's upper airway when the image pickup apparatus 20c is put into the patient's upper airway. The display unit 25c may be an LCD panel or other flat panel display and may be installed on the handgrip of the image pickup apparatus 20c for displaying the image captured by the image-capturing unit 22c. The memory unit 26c may be a memory chip and is electrically connected to the image-capturing unit 22c for storing the image captured by the image-capturing unit 22c. In addition, if users prefer to observe the image captured by the image-capturing unit 22c in greater detail on an external display 30, the image pickup apparatus 20c may further include the signal emission unit 27c for transmitting the image captured by the image-capturing unit 22c to the external display 30 wirelessly.

Figure 11:
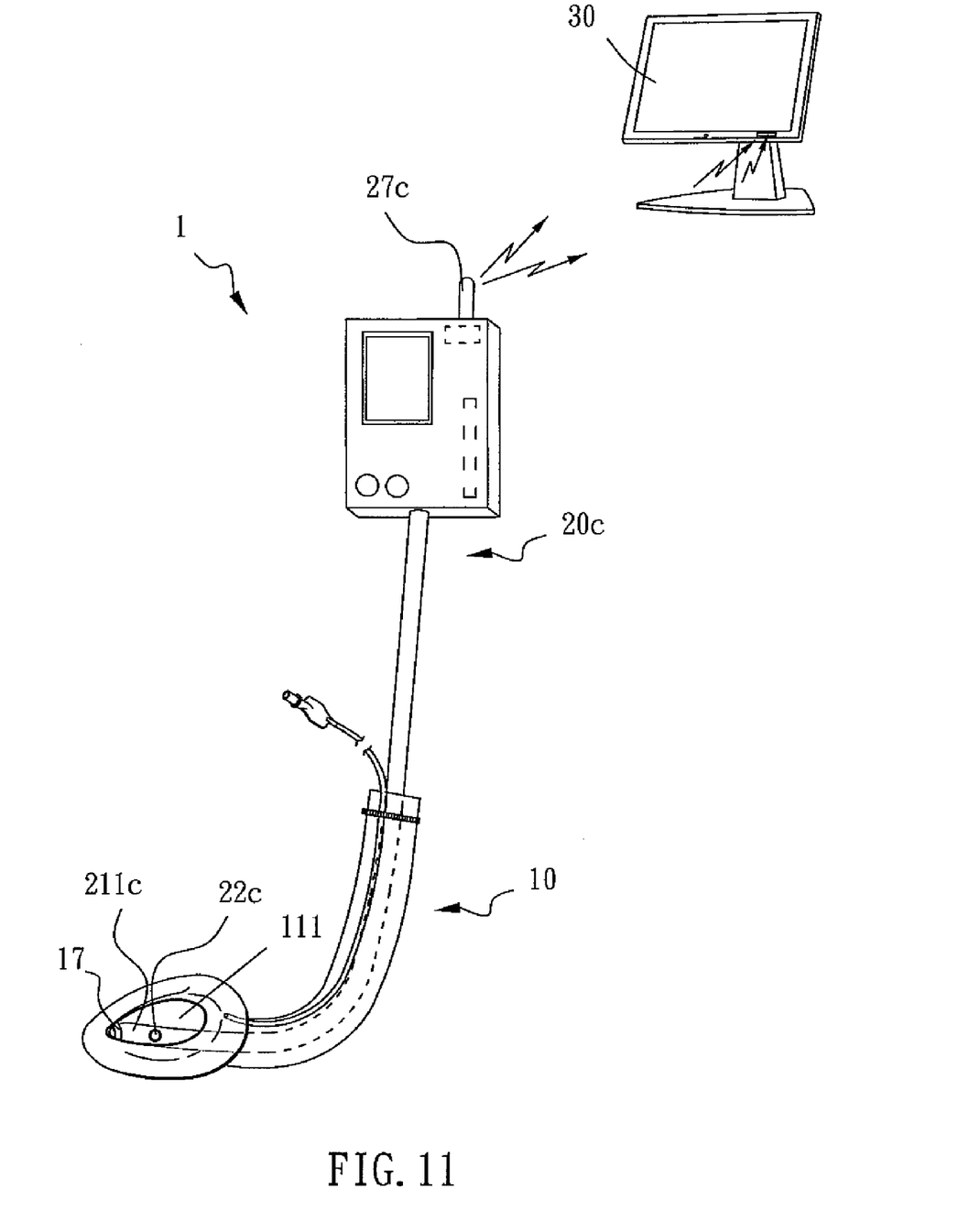
FIG. 11 illustrates the gas supply kit of the present invention.

Last but not least, please refer to FIG. 11 for an illustration of the gas supply kit 1 of the present invention. The gas supply kit 1 comprises a laryngeal mask airway 10 and an operating piece 20. The operating piece 20 may be a metal bar 20a, a hollow tube 20b, or, as shown in this embodiment, an image pickup apparatus 20c. The laryngeal mask airway 10 has a belt 17 where the propping end 211c of the image pickup apparatus 20c may be leaned so as to bend the laryngeal mask airway 10 to the extent in conformity with the radian of a human oral airway. In addition, the image pickup apparatus 20c also comprises an image-capturing unit 22c. When the image pickup apparatus 20c is inserted into the laryngeal mask airway 10, the image-capturing unit 22c may be located at the first opening part 111 of the laryngeal mask airway 10. In that way, the image-capturing unit 22c is capable of capturing the image of the patient's upper airway when the laryngeal mask airway 10 is placed thereinto. In addition, the image pickup apparatus 20c may comprise a signal emission unit 27c as well for transmitting the image captured by the image-capturing unit 22c to an external display 30 wirelessly so as to enable a user to observe the patient's condition thereby.

It will be understood that many other modifications can be made to the various disclosed embodiments without departing from the spirit and scope of the invention. For these reasons, the above description should not be construed as limiting the invention, but should be interpreted as merely exemplary of preferred embodiments.

What is claimed is:

1. An operating piece used together with a laryngeal mask airway having a belt, said operating piece comprising one end pressed against the belt to change the shape of the laryngeal mask airway, wherein a curvature of the operating piece is in conformity with a radian of a human oral airway, with said operating piece being an image pickup apparatus which comprises:
 a steel pipe comprising a propping end and a handling end, with said propping end being capable of applying pressure to the belt;
 an image-capturing unit installed on the steel pipe, with said image-capturing unit being capable of capturing an image of a patient's upper airway; and
 a handgrip installed at the handling end, with said handgrip comprising a power supply electrically connected to the image-capturing unit for providing electricity thereto.

2. The operating piece as claimed in claim 1, with said operating piece being a metal bar.

3. The operating piece as claimed in claim 1, with said operating piece being a hollow tube.

4. The operating piece as claimed in claim 3, wherein the operating piece has a bore drilled therein.

5. The operating piece as claimed in claim 1, wherein the image pickup apparatus further comprises a display unit electrically connected to the image-capturing unit for displaying the image captured by the image-capturing unit.

6. The operating piece as claimed in claim 1, wherein the image pickup apparatus further comprises a memory unit electrically connected to the image-capturing unit for storing the image captured by the image-capturing unit.

7. The operating piece as claimed in claim 1, wherein the image pickup apparatus further comprises a signal emission unit electrically connected to the image-capturing unit for transmitting the image captured by the image-capturing unit to an external display wirelessly.

8. A gas supply kit comprising:
(a) a laryngeal mask airway comprising:
(1) a tubular portion comprising a first opening part and a second opening part;
(2) an inflatable sealing cuff surrounding the first opening part;
(3) an inflation tube comprising one end connected to the inflatable sealing cuff and another end directing gas into the inflatable sealing cuff; and
(4) a belt secured on the first opening part; and
(b) an operating piece inserted in the tubular portion, with said operating piece being capable of leaning against the belt to change a shape of the laryngeal mask airway, wherein the curvature of the operating piece is in conformity with a radian of a human oral airway.

9. The gas supply kit as claimed in claim 8, wherein the belt is substantially secured at a tip of the first opening part.

10. The gas supply kit as claimed in claim 8, wherein the operating piece is a metal bar.

11. The gas supply kit as claimed in claim 8, wherein the operating piece is a hollow tube.

12. The gas supply kit as claimed in claim 11, wherein the operating piece has a bore drilled therein.

13. The gas supply kit as claimed in claim 8, wherein the operating piece is an image pickup apparatus which comprises:
a steel pipe comprising a propping end and a handling end, with said propping end pressing against the belt;
an image-capturing unit installed on the steel pipe, with said image-capturing unit being capable of capturing an image of a patient's upper airway; and
a handgrip installed at the handling end, with said handgrip comprising a power supply electrically connected to the image-capturing unit for providing electricity thereto.

14. gas supply kit as claimed in claim 13, wherein the image pickup apparatus further comprises a display unit electrically connected to the image-capturing unit for displaying the image captured by the image-capturing unit.

15. The gas supply kit as claimed in claim 13, wherein the image pickup apparatus further comprises a memory unit electrically connected to the image-capturing unit for storing the image captured by the image-capturing unit.

16. The gas supply kit as claimed in claim 13, wherein the image pickup apparatus further comprises a signal emission unit electrically connected to the image-capturing unit for transmitting the image captured by the image-capturing unit to an external display wirelessly.

* * * * *